United States Patent [19]

Stoss et al.

[11] 3,951,997

[45] Apr. 20, 1976

[54] CYCLIC SULPHOXIMIDES

[75] Inventors: Peter Stoss, Wildtal; Gerhard Satzinger, Denzlingen, both of Germany

[73] Assignee: Warner-Lambert Company, Morris Plains, N.J.

[22] Filed: Aug. 9, 1974

[21] Appl. No.: 495,984

[30] Foreign Application Priority Data

Aug. 11, 1973 Germany............................ 2340815

[52] U.S. Cl............................. 260/304 A; 424/270
[51] Int. Cl.².................................... C07D 275/04
[58] Field of Search............................ 260/302, 304

[56] References Cited
OTHER PUBLICATIONS

Chem. Abstracts, 1967, Vol. 67, p. 1000567z.
Chem. Berichte, 1970, Vol. 103, pp. 3166–3181.

*Primary Examiner*—Dale R. Ore
*Attorney, Agent, or Firm*—Albert H. Graddis; Frank S. Chow; George M. Yahwak

[57] ABSTRACT

The present invention is concerned with novel cyclic sulphoximides and their preparation. These novel compounds are intermediates for a series of novel cyclic sulphoximides which show pharmaceutical activity.

7 Claims, No Drawings

CYCLIC SULPHOXIMIDES

The cyclic sulphoximides have previously not been investigated to any great extent. The known compounds of this type include a few 5-membered cyclic sulphoximides (see German Patent Specification No. 1,914,016; Angew. Chem., 83, 83/1971; J.A.C.S., 93, 7333/1971; J. Org. Chem., 38, 20/1973) but the compounds described in these literature references do not contain suitable functional groups so that they are not capable of modification by substitution or further reaction.

The present invention relates to novel cyclic sulphoximides which contain a functional group capable of chemical reaction to form cyclic sulphoximide derivatives. These derivatives possess valuable pharmacological activity and are disclosed in U.S. Ser. No. 495,985, filed Aug. 9, 1974 in the name of Stoss, Satzinger and Herrmann.

Thus, according to the present invention, there are provided new cyclic sulphoximides of the general formula:

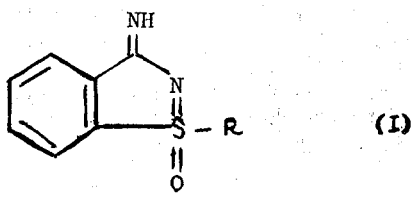

wherein R is a lower alkyl or phenyl radical, as well as salts with inorganic and organic acids.

The new compounds of general formula (I) according to the present invention can be substituted on the imino group, for example by acyl radicals; the N-substituted compounds thus obtained being valuable pharmaceuticals with an anti-inflammatory and analgesic action.

Since the imino group of the new compounds of general formula (I) is capable of undergoing a large variety of chemical reactions, these new compounds are valuable intermediates for the preparation of pharmaceutical compounds.

As lower alkyl radicals in the compounds of general formula (I), there are to be understood straight-chained or branched aliphatic radicals containing up to 4 carbon atoms, for example methyl, ethyl, n-propyl, isopropyl, n-butyl and sec.-butyl radicals; the methyl radical being preferred.

The novel compounds (I) according to the present invention can be prepared by reacting a compound of the general formula:

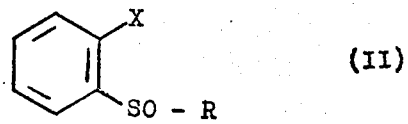

wherein R has the same meaning as above and X is a nitrile or amido group, and in the presence of a strong acid, with hydrazoic acid or with a salt thereof.

As strong acids, there can be used sulphuric acid, phosphoric acid or, preferably, polyphosphoric acid or a mixture of phosphoric acid with phosphorus pentoxide.

The reaction of the compounds (II) can be carried out at a temperature of between about 50° and 150°C. and preferably at a temperature of between 80° and 100°C.

Since the strong acid used in the reaction can also liberate hydrazoic acid from salts thereof, it is generally preferred to use an alkali metal or alkaline earth metal salt of hydrazoic acid, which are easier to handle.

The compounds of general formula (I) can be isolated either as salts of the acid used for the reaction or the free base can be obtained from an alkaline medium and this converted into the salt by the addition of an acid, such as hydrochloric, hydrobromic, acetic, oxalic, salicylic, succinic, malic, or the like.

The compounds of general formula (II) in which X is an amido group are also new. They can be obtained by the oxidation of the corresponding sulphide with an appropriate oxidation agent, for example, a periodate or hydrogen peroxide.

The reaction of the compounds of general formula (II) with hydrazoic acid to give the compounds of general formula (I) was unexpected. According to the prior art, an analogous reaction of 2-sulphinylaryl-carboxylic acids or of their esters always resulted in the splitting off of water or of an alochol, to give 3-oxo-1,2-benziso-thiazole-1-oxides, i.e. the carboxyl oxygen of the starting material remains in the end product obtained. In contradistinction thereto, according to the process of the present invention, the carbonyl function of the amido group is, surprisingly, eliminated. Nothing is known regarding an analogous reaction of nitriles so that this variant must also be regarded as being chemically novel.

The folllowing Examples are given for the purpose of illustrating the present invention:

EXAMPLE 1

3H-3-Imino-1-methyl-1,2-benzisothiazole-1-oxide

Variant A

A mixture of 150 g. phosphoric acid, 100 g. phosphorus pentoxide and 36.6 g. 2-methyl-sulphinylbenzamide is heated to 90°C. 26 g. sodium azide are introduced portionwise, while stirring, over the course of an hour. Thereafter, the reaction mixture is stirred for a further 4 hours at 95°C., then cooled and the reaction mixture rendered alkaline with a saturated aqueous solution of potassium hydroxide. By shaking out with chloroform, there is extracted the 3H-3-imino-1-methyl-1,2-benzisothiazole-1-oxide. The chloroform solution is dried and evaporated to give the product in the form of an oily residue which crystallizes upon rubbing. After recrystallization from ethyl acetate, the product is obtained in the form of pale yellow crystals; m.p. 125°C.

The compound can be converted into its hydrochloride by reaction with hydrogen chloride in an appropriate solvent. The hydrochloride is obtained in the form of colorless crystals, after recrystallization from ethanol; m.p. 186°C. (decomp.).

The 2-methyl-sulphinylbenzamide used as starting material is prepared as follows:

A solution of 184 g. sodium periodate in 1.7 liters water is added dropwise, while stirring, to a solution of 126 g. 2-methylthiobenzamide in 4 liters methanol, whereafter the reaction mixture is further stirred for 24 hours. The precipitated sodium iodate is filtered off with suction and adhering reaction product is removed therefrom by washing with methanol. The bulk of the methanol is evaporated from the filtrate, the greater part of the reaction product thereby crystallizing out. It is filtered off with suction and the aqueous filtrate continuously extracted with ethyl acetate. The evaporation residue of this extract, together with the reaction product previously filtered off with suction, are recrystallized from isopropanol. There is thus obtained pure 2-methyl-sulphinylbenzamide in the form of colorless crystals; m.p. 192°–193°C.

Variant B

A mixture of 150 g. phosphoric acid, 100 g. phosphorus pentoxide and 33.8 g. 2-methyl-sulphinylbenzonitrile is heated to 90°C. and mixed portionwise with 26 g. sodium azide over the course of an hour. After 4 hours, the reaction mixture is further worked up in the manner described in Variant A. There is thus obtained pure 3H-3-imino-1-methyl-1,2-benzisothiazole-1-oxide; m.p. 125°C.

The 2-methyl-sulphinylbenzonitrile used as starting material is prepared in the manner described in Chem. Abs., 71, 3099r/1969.

EXAMPLE 2

3H-3-Imino-1-phenyl-1,2-benzisothiazole-1-oxide 48 g. 2-(phenylsulphinyl)-benzamide are reacted in 300 g. phoshphoric acid and 160 g. phosphorus pentoxide with 28 g. sodium azide in a manner analogous to that described in Example 1. 3H-3-imino-1-phenyl-1,2-benzisothiazole-1-oxide is obtained in the form of colorless crystals which, after recrystallization from ethyl acetate/isopropanol, melt at 178°C.

The 2-(phenylsulphinyl)-benzamide used as starting material is obtained by the oxidation of 2-phenylthiobenzamide with perhydrol (hydrogen peroxide) in glacial acetic acid. After recrystallization from methanol, it melts at 213°C.

Structurally, these compounds are:

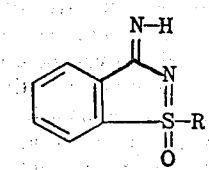

| Example | R | Salt | melting point (°C) |
|---|---|---|---|
| 1 | methyl | — | 125 |
|  |  | hydrochloride | 186 |
| 2 | phenyl | — | 178 |

We claim:
1. Cyclic sulphoximide of the formula:

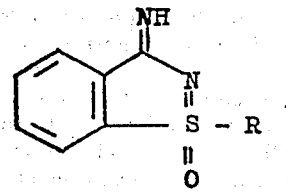

wherein R is a lower alkyl of 1 to 4 carbon atoms or phenyl, and pharmaceutically acceptable acid salts thereof.

2. The sulphoximide of claim 1 wherein R is methyl and which is 3H-3-imino-1-methyl-1,2-benzisothiazole-1-oxide.

3. The sulphoximide of claim 1 wherein R is phenyl and which is 3H-3-imino-1-phenyl-1,2-benzoisothiazole-1-oxide.

4. Process for the preparation of cyclic sulphoximide of the formula given in claim 1, wherein a compound of the formula:

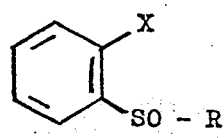

in which R is lower alkyl of 1 to 4 carbon atoms or phenyl and X is a nitrile or amido group, is reacted at temperature of between about 50° and 150°C with hydrazoic acid in the presence of a strong acid.

5. Process according to claim 4, wherein the strong acid is sulphuric acid, phosphoric acid, polyphosphoric acid or a mixture of phosphoric acid and phosphorus pentoxide.

6. Process according to claim 1, wherein the reaction is carried out at a temperature of between 80° and 100°C.

7. Process according to claim 6 wherein the cyclic sulphoximide is isolated from the reaction mixture in the form of a salt with the strong acid used for the reaction or is isolated from an alkaline medium in the form of the free base and, if desired, subsequently reacted with an inorganic or organic acid to form the corresponding salt.

* * * * *